(12) United States Patent
Matsumura et al.

(10) Patent No.: US 9,468,688 B2
(45) Date of Patent: Oct. 18, 2016

(54) BORON CLUSTER-MODIFIED PEG LIPID DERIVATIVE, AND MOLECULAR ASSEMBLY USING SAME

(71) Applicant: UNIVERSITY OF TSUKUBA, Tsukuba-shi, Ibaraki (JP)

(72) Inventors: Akira Matsumura, Ibaraki (JP); Kei Nakai, Ibaraki (JP); Makoto Shirakawa, Ibaraki (JP)

(73) Assignee: UNIVERSITY OF TSUKUBA, Tsukuba-shi (JP)

( * ) Notice: Subject to any disclaimer, the term of this patent is extended or adjusted under 35 U.S.C. 154(b) by 0 days.

(21) Appl. No.: 14/423,049

(22) PCT Filed: Aug. 22, 2013

(86) PCT No.: PCT/JP2013/072458
§ 371 (c)(1),
(2) Date: Feb. 20, 2015

(87) PCT Pub. No.: WO2014/030715
PCT Pub. Date: Feb. 27, 2014

(65) Prior Publication Data
US 2015/0238622 A1 Aug. 27, 2015

(30) Foreign Application Priority Data
Aug. 23, 2012 (JP) ................................ 2012-184283

(51) Int. Cl.
| | | |
|---|---|---|
| A61K 47/48 | (2006.01) | |
| A61K 33/22 | (2006.01) | |
| A61K 31/69 | (2006.01) | |
| C07F 9/572 | (2006.01) | |
| C07F 9/10 | (2006.01) | |
| C08G 65/328 | (2006.01) | |
| A61K 9/127 | (2006.01) | |
| A61K 41/00 | (2006.01) | |

(52) U.S. Cl.
CPC ....... *A61K 47/48215* (2013.01); *A61K 9/1271* (2013.01); *A61K 31/69* (2013.01); *A61K 33/22* (2013.01); *A61K 41/0095* (2013.01); *A61K 47/48053* (2013.01); *A61K 47/48123* (2013.01); *C07F 9/106* (2013.01); *C07F 9/5721* (2013.01); *C08G 65/328* (2013.01); *A61K 47/48815* (2013.01)

(58) Field of Classification Search
None
See application file for complete search history.

(56) References Cited

FOREIGN PATENT DOCUMENTS

| | | |
|---|---|---|
| JP | 2005-343858 A | 12/2005 |
| JP | 2008-13498 A | 1/2008 |
| JP | 2008-94730 A | 4/2008 |

OTHER PUBLICATIONS

Ueno M, Dodecaborate lipid liposomes as new vehicles for boron delivery system of neutron capture therapy, Bioorganic and Medicinal Chemistry, 18, 2010, 3059-3065.*
Hiroyuki Nakamura, "Minimally Invasive Cytoselective Radiation Therapy Using Boron Neutron Capture Reaction", Yakugaku Zasshi, 2010, pp. 1687-1694, vol. 130, No. 12.
International Search Report issued in PCT/JP2013/072458, dated Nov. 26, 2013.
Jong-Dae Lee et al., Synthesis of Boron Cluster Lipids: closo-Dodecaborate as an Alternative Hydrophilic Function of Boronated Liposomes for Neutron Capture Therapy, Org. Lett, American Chemical Society, Jan. 18, 2007, pp. 323-326, vol. 9, No. 2.
Kazuo Maruyama et al., "Intracellular targeting of sodium mercaptoundecahydrododecaborate (BSH) to solid tumors by transferrin-PEG liposomes, for boron neutron-capture therapy (BNCT)", Journal of Controlled Release 98 (2), Aug. 11, 2004, pp. 195-207.
Manabu Ueno et al., "Dodecaborate lipid liposomes as new vehicles for boron delivery system of neutron capture therapy", Bioorganic & Medicinal Chemistry 18, 2010, pp. 3059-3065, vol. 18, No. 9.
Tetsuya Yamamoto et al., "Boron neutron capture therapy for newly diagnosed glioblastoma", Radiotherapy and Oncology 91 (1), Apr. 2009, pp. 80-84, Epub Mar. 11, 2009.

* cited by examiner

*Primary Examiner* — Frederick Krass
*Assistant Examiner* — Celeste A Roney
(74) *Attorney, Agent, or Firm* — Birch, Stewart, Kolasch & Birch, LLP

(57) ABSTRACT

The present invention provides a novel boron carrier compound that can be used for boron neutron capture therapy for cancer, and that can realize improvement in the efficiency of a Drug Delivery System (DDS) and an increase in the boron concentration in a tumor. The present invention provides a boron cluster-modified PEG lipid derivative represented by Formula (I):

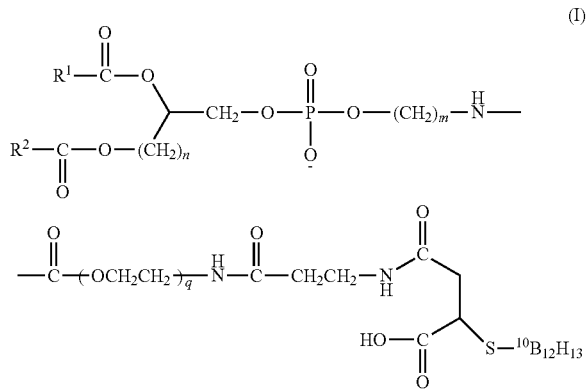

wherein, m and n are each independently an integer of 1-4, q is an integer of 1-280, and $R^1$ and $R^2$ are each independently a hydrocarbon group with a carbon number of 8-22, and a molecular assembly containing the same.

16 Claims, 13 Drawing Sheets
(3 of 13 Drawing Sheet(s) Filed in Color)

| No. | Ch | 1 | 2 | 3 | 4 | 5 | 6 | 7 | 8 |
|---|---|---|---|---|---|---|---|---|---|
| 1 | 1 | 9.717 | 31.13 | 4.23 | 144.16 | 0.69 | 105428 | 0.00 | 1.26 |
| 2 | 1 | 10.548 | 108.74 | 4.40 | 509.52 | 2.45 | 114451 | 6.81 | 0.00 |
| 3 | 1 | 10.688 | 76.46 | 4.47 | 356.60 | 1.71 | 114072 | 1.12 | 0.00 |
| 4 | 1 | 10.763 | 16.43 | 0.00 | 58.79 | 0.28 | 0 | 0.00 | 0.00 |
| 5 | 1 | 10.940 | 4.52 | 0.00 | 27.97 | 0.13 | 0 | 0.00 | 0.00 |
| 6 | 1 | 11.533 | 9.75 | 3.67 | 48.08 | 0.23 | 197007 | 0.00 | 0.48 |
| 7 | 1 | 11.700 | 1.46 | 4.71 | 8.04 | 0.04 | 122928 | 1.41 | 1.53 |
| 8 | 1 | 12.685 | 1.58 | 3.17 | 5.27 | 0.03 | 320268 | 8.84 | 1.33 |
| 9 | 1 | 12.918 | 1.36 | 3.41 | 4.86 | 0.02 | 286645 | 2.51 | 1.32 |
| 10 | 1 | 13.448 | 24.72 | 3.56 | 95.24 | 0.46 | 284167 | 5.37 | 1.29 |
| 11 | 1 | 14.238 | 948.25 | 17.38 | 17013.82 | 81.71 | 13386 | 2.67 | 4.60 |
| 12 | 1 | 14.952 | 157.66 | 9.51 | 1707.81 | 8.20 | 49306 | 1.88 | 0.00 |
| 13 | 1 | 15.813 | 26.40 | 3.06 | 91.52 | 0.44 | 533940 | 4.85 | 1.46 |
| 14 | 1 | 16.370 | 52.77 | 11.22 | 751.74 | 3.61 | 42437 | 2.76 | 6.02 |
|   |   |   | 1461.23 |   | 20823.40 | 100.00 |   |   |   |

1 Time [min.]
2 Height
3 Half width [sec.]
4 Area [mV x sec.]
5 Area %
6 Number of theoretical plate
7 Separability
8 Dissymmetry coefficient
9 Column
10 Detector
11 Detection condition
12 Injection volume
13 Pressure
14 Column temperature
15 Eluent
16 Gradient conditions 9 : Supeico Discovery HS C18 4.6mm I.D. x7.5cm Particle 3μm
10 : UV-8020
11 : 220nm
12 : 100
13 : 6.9
14 : 45.0
15 : A:0. 1%TFA B:0. 1%TFA+ACN
16 : 5%--2min--5% - 5%--12min--80%

BORON CLUSTER-MODIFIED PEG LIPID DERIVATIVE, AND MOLECULAR ASSEMBLY USING SAME

TECHNICAL FIELD

The present invention relates to a PEG lipid derivative useful as a drug carrier that selectively accumulates in a tumor tissue and delivering boron, and a molecular assembly using the same.

BACKGROUND ART

Boron neutron capture therapy (hereinafter, also referred to as "BNCT") for cancer is a radiation therapy that impairs tumor cells with alpha particles and $^7$Li particles that result through the capture reaction between $^{10}$B nucleus that has been taken up by the tumor tissues and a thermal neutron beam that generally does not affect the body. Since the pathway of the particle radiation resulting from this nuclear reaction is almost equal to the diameter of the cell, if boron can be accumulated only in the tumor tissues at a high concentration in advance, they can be irradiated with thermal neutron so that the tumor tissues can cell-selectively impaired with a minimum damage on normal tissues. Accordingly, therapeutic effects can be expected even in tumors that are less susceptible to radiation or in infiltrative tumors. Clinical studies have been conducted on recurrent cases of malignant brain tumor (glioblastoma) and head and neck cancer that are clinically infiltrative and that have adverse prognosis, and good results have been reported (Non-patent Document 1).

A clinically used boron compound is a monomolecular compound of boronophenylalanine (BPA) and a boron ion cluster called BSH. Although these compounds have been clinically applied, they are not adequate in terms of accumulation in the tumors and thus the attempt to further enhance the boron concentration ratio in tumor and normal tissues (T/N ratio) has been continued. In addition, techniques for entrapping a hydrophilic boron compound such as BHA ($^{10}$B-enriched 4-Borono-L-phenylalanine, $C_9H_{12}{}^{10}BNO_4$) or BSH ($^{10}$B-enriched Sodium mercaptodo-decaborate, BSH [CAS No. 12448-24-7], [$^{10}B_{12}H_{11}SH$] $Na_2$) into a liposome whose surface has been covered by polyethylene glycol (PEG) are used as a technique for accumulating a high concentration of boron only in the tumor tissues (Non-patent Document 2).

However, according to these methods, there have been major issues of radiation damage on the normal tissues caused by boron in the normal tissues and poor therapeutic effect due to incompatibility between difficulty in accumulating boron to an effective therapeutic range and accomplishment of targeted T/N ratio.

Another technique has also been developed in which a boron compound is entrapped in a phospholipid bilayer through covalent bonding between a lipid and an aqueous boron compound. However, this requires multiple and complicated steps for synthesis, and thus numbers of problems remain in terms of efficiency and cost. Moreover, several cases of acute toxicity have been reported in animal experiments, leaving problems also in terms of safety (Non-patent Document 3).

PRIOR ART DOCUMENTS

Non-Patent Documents

Non-patent Document 1: *Boron neutron capture therapy for newly diagnosed glioblastoma*, Yamamoto T, Nakai K, Kageji T, Kumada H, Endo K, Matsuda M, Shibata Y, Matsumura A., Radiother Oncol. 2009 April; 91(1):80-4. Epub 2009 Mar. 11.

Non-patent Document 2: *Intracellular targeting of sodium mercaptoundecahydrododecaborate (BSH) to solid tumors by transferrin-PEG liposomes, for boron neutron-capture therapy (BNCT)*, Maruyama K, Ishida O, Kasaoka S, Takizawa T, Utoguchi N, Shinohara A, Chiba M, Kobayashi H, Eriguchi M, Yanagie H., J Control Release. 2004 Aug. 11; 98(2):195-207.

Non-patent Document 3: *Synthesis of boron cluster lipids: closo-dodecaborate as an alternative hydrophilic function of boronated liposomes for neutron capture therapy*, Lee JD, Ueno M, Miyajima Y, Nakamura H., Org Lett. 2007 Jan. 18; 9(2):323-6.

SUMMARY OF THE INVENTION

Problems to be Solved by the Invention

Currently, general properties required as a boron compound to be used for the boron neutron capture therapy are as follows.

i) $^{10}$B concentration of at least 20 ug/g or more can be achieved in a tumor. ii) Meanwhile, $^{10}$B concentration is as low as possible in normal tissues. iii) A tumor/blood ratio is preferably 5-10 or higher.

In order to achieve this concentration, unlike general pharmaceutical products, the boron compound needs to be administered into the body at a high dose. Therefore, it is important that the toxicity of the boron compound is low so that it can be used in the boron neutron capture therapy. In the case of the currently existing compound BSH or BPA, 5 g or 15-25 g per human adult, respectively, needs to be used by a bolus intravenous administration, which is 10-100 times more than the weight of a general pharmaceutical product.

Under such circumstances, there have been needs for improvement in the efficiency of a Drug Delivery System (DDS) that can be used for boron neutron capture therapy for cancer, an increase in the boron concentration in a tumor, and a novel boron carrier compound that can realize low toxicity.

Means for Solving the Problems

In order to solve the above-described problem, the present inventors have gone through intensive studies and found that boron modification of a lipid building up a molecular assembly has a high chance of realizing an increase in the boron concentration in a tumor as well as lower boron accumulation in a normal cell upon use of DDS, thereby accomplishing the present invention.

Thus, the present invention relates to a boron cluster-modified PEG lipid derivative stated below and a molecular assembly containing the same.

[1] A boron cluster-modified PEG lipid derivative represented by Formula (I):

[Chemical Formula 1]

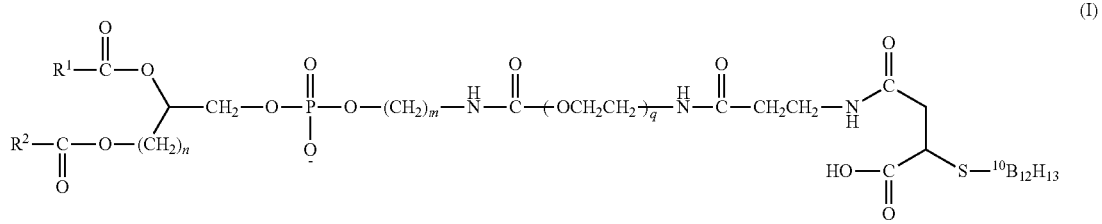

wherein, m and n are each independently an integer of 1-4, q is an integer of 1-280, and $R^1$ and $R^2$ are each independently a hydrocarbon group with a carbon number of 8-22.

[2] The PEG lipid derivative according to [1], wherein $R^1$ and $R^2$ are each independently a linear or branched alkyl group with a carbon number of 12-22.

[3] The PEG lipid derivative according to either one of [1] and [2], wherein m is 2 and n is 1.

[4] A molecular assembly comprising the PEG lipid derivative according to any one of [1] to [3].

[5] The molecular assembly according to [4], wherein the PEG lipid derivative is contained at 2-20% in a molar ratio with respect to the total structural lipid of the molecular assembly.

[6] The molecular assembly according to either one of [4] and [5], further comprising L-α-phosphatidylcholine distearoyl and cholesterol.

[7] The molecular assembly according to any one of [4] to [6], which is a liposome.

[8] The molecular assembly according to [7], wherein the particle size of the liposome is 50-400 nm as measured by a dynamic light scattering method.

Effect of the Invention

The present invention can provide a novel boron carrier compound that can be used for boron neutron capture therapy for cancer. According to a preferable embodiment of the present invention, use of a molecular assembly containing the boron cluster-modified PEG lipid derivative of the present invention is highly possible to realize an increase in the boron concentration in a tumor and lower boron accumulation in normal cells upon use of DDS. The present inventors have confirmed that no acute toxicity was caused up to a boron concentration of 2000 ppm (215.6 mg/ml in terms of lipid concentration) and further that no abnormality was found upon physical observation. Accordingly, the molecular assembly of the present invention is a boron carrier compound that has low toxicity and that can favorably used for boron neutron capture therapy.

BRIEF DESCRIPTION OF THE DRAWINGS

The patent or application file contains at least one color drawing. Copies of this patent or patent application publication with color drawings will be provided by the USPTO upon request and payment of the necessary fee.

EMBODIMENTS FOR CARRYING OUT THE INVENTION

Figure 1:
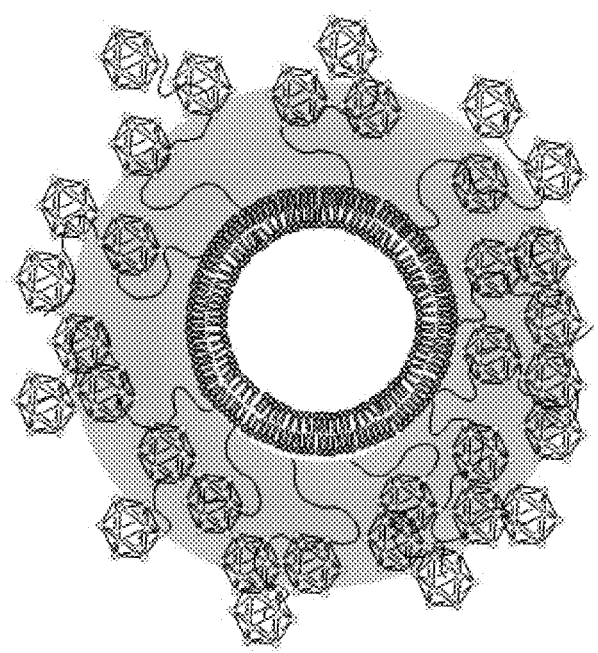
FIG. 1 A conceptual diagram of a liposome containing a boron cluster-modified PEG lipid derivative according to one embodiment of the present invention.

Hereinafter, a boron cluster-modified PEG lipid derivative of the present invention and a molecular assembly containing the same will be described in detail.

1. Boron Cluster-Modified PEG Lipid Derivative

A boron cluster-modified PEG lipid derivative of the present invention is a compound represented by Formula (I):

[Chemical Formula 2]

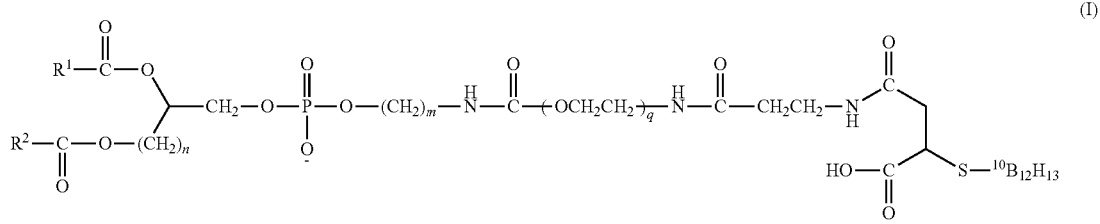

(I)

wherein, m and n are each independently an integer of 1-4, q is an integer of 1-280, $R^1$ and $R^2$ are each independently a hydrocarbon group with a carbon number of 8-22.

The boron cluster-modified PEG lipid derivative of the present invention has a structure in which a PEG lipid is modified with a boron cluster ($^{10}B_{12}H_{13}$). Therefore, it can be used as a structural lipid of a molecular assembly such as a liposome and can be used as a boron carrier compound used for BNCT.

In the formula, m and n are each independently an integer of 1-4, and preferably 1 or 2. For the sake of easier availability of the raw material, m is preferably 2 and n is preferably 1.

q is an integer of 1-280, preferably an integer of 10-114, and more preferably an integer of 44-66. Within this range, the retentivity in blood can be most achieved due to steric hindrance resulting from the thickness and movement of the hydrated phase caused by PEG.

$R^1$ and $R^2$ are each independently a hydrocarbon group with a carbon number of 8-22. The hydrocarbon group may be either linear or branched, but preferably linear. Moreover, the hydrocarbon group may have a substituent selected from the group consisting of a carboxyl group, a hydroxyl group, an amino group and a mercapto group. The carbon number of the hydrocarbon group is preferably 12-20, and more preferably 14-18. The hydrocarbon group may have an unsaturated bond such as a double bond or a triple bond, in which case the number thereof is preferably 1-4. Among them, $R^1$ and $R^2$ are preferably a linear or branched alkyl group with a carbon number of 12-22, more preferably a linear alkyl group with a carbon number of 14-18, and particularly preferably a linear alkyl group with a carbon number of 17.

The boron cluster-modified PEG lipid derivative of the present invention can simply be produced by allowing a reaction between a maleimide derivative represented by Formula (II):

wherein m, n, q, $R^1$ and $R^2$ are synonymous with those in Formula (I), and $^{10}B$ enriched Sodium mercaptododecaborate (BSH) [CAS No. 12448-24-7], [$^{10}B_{12}H_{11}SH]Na_2$ commercially available from Katchem spol. s r. o., Ltd. in a phosphate buffered saline.

After the reaction, the resultant is freeze-dried. Thereafter, the crude product is dissolved in ultrapure water, dialyzed to enhance purity thereof, and freeze-dried, thereby obtaining a compound of interest.

The compound represented by Formula (II) can be produced by introducing a hydrophobic alkyl chain into, for example, a terminal of amino acids to give a transmembrane domain, and linking maleimide PEG to the terminal thereof. Alternatively, the compound represented by Formula (II) may be a commercially available product. Examples include SUNBRIGHT (registered trademark) SERIES DSPE-020MA, DSPE-050MA, DSPE-PEG-MAL (compound name: N-[(3-Maleimide-1-oxopropyl)aminopropyl polyethyleneglycol-carbamyl]distearoylphosphatidyl-ethanolamine) available from NOF CORPORATION, and DEPE-PEG (2000) Maleimide (compound name: 1,2-distearoyl-sn-glycero-3-phosphoethanolamine-N-[mal(polyethylene glycol)-2000] (ammonium salt)) available from Avanti Polar Lipids.

The boron cluster-modified PEG lipid derivative of the present invention can be used as a structural lipid of a molecular assembly.

2. Molecular Assembly

The molecular assembly of the present invention is not particularly limited as long as it contains the above-described boron cluster-modified PEG lipid derivative as a structural lipid.

Although the quantity of the boron cluster-modified PEG lipid derivative used for the molecular assembly of the present invention is not particularly limited, it is preferably 2-20%, more preferably 3-15% and still more preferably 5-10% in a molar ratio with respect to the total structural

[Chemical Formula 3]

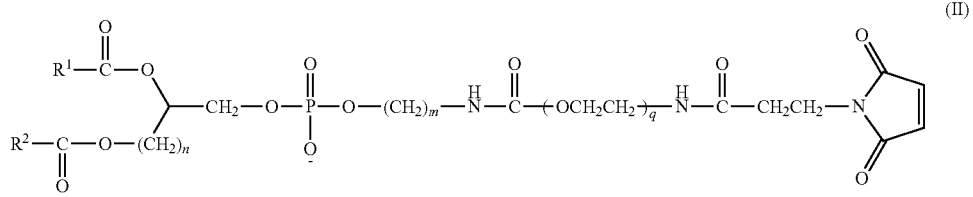

(II)

lipid of the molecular assembly. The quantity of the boron cluster-modified PEG lipid derivative can suitably be adjusted to control the concentration of boron in the tumor according to the intended use.

The molecular assembly of the present invention may also contain other structural lipid apart from the boron cluster-modified PEG lipid derivative.

Examples of other structural lipid include phospholipid, for example, glycerophospholipids such as phosphatidylcholine (dimyristoylphosphatidylcholine (DMPC), L-α-phosphatidylcholine distearoyl (DSPC), etc.), phosphatidylethanolamine, phosphatidylserine, phosphatidic acid, phosphatidylglycerol, phosphatidylinositol, Cardiolipin, egg-yolk lecithin, hydrogenated egg-yolk lecithin, soybean lecithin and hydrogenated soybean lecithin; and sphingophospholipids such as sphingomyelin, ceramide phosphorylethanolamine and ceramide phosphorylglycerol. Among them, phosphatidylcholine is preferable, and L-α-phosphatidylcholine distearoyl (DSPC) is particularly preferable.

The quantity of the phospholipid used for the molecular assembly of the present invention is preferably 40-95%, more preferably 40-70% and still more preferably 40-50% in a molar ratio with respect to the total structural lipid of the molecular assembly.

Further examples of other structural lipid include steroids. Examples of steroids include ergosterol, cholesterol and triglyceride. Among them, cholesterol is preferable.

The quantity of steroids used for the molecular assembly of the present invention is preferably 0-50%, more preferably 30-50% and still more preferably 40-50% in a molar ratio with respect to the total structural lipid of the molecular assembly.

The molecular assembly of the present invention may further comprise glycolipids, for example, glyceroglycolipids such as digalactosyldiglyceride and galactoxyldiglyceride sulfate; and sphingoglycolipids such as galactosylceramide, galactosylceramide sulfate, lactosylceramide, ganglioside G7, ganglioside G6 and ganglioside G4. Among them, ganglioside G4 is preferable.

The quantity of the glycolipid is preferably 4-24% in a molar ratio with respect to the total structural lipid of the molecular assembly.

The form of the molecular assembly of the present invention may, for example, be a polymeric assembly, a polymeric micelle, emulsion, lipid microsphere, a bilayer vesicle (liposome), other molecular assembly (tube, fiber, ribbon, sheet, etc.). Among them, the molecular assembly of the present invention is preferably in a form of a liposome.

FIG. 1 is a conceptual diagram of a liposome containing a boron cluster-modified PEG lipid derivative according to one embodiment of the present invention. As shown in FIG. 1, in the liposome of the present invention, the surface of the lipid bilayer vesicle formed of a structural lipid is surrounded by PEG, whose surface, in turn, is bound to boron clusters.

When the molecular assembly of the present invention is a liposome, the particle size of the liposome is preferably 50-400 nm, more preferably 50-200 nm and still more preferably 100-200 nm as measured by a dynamic light scattering method.

The molecular assembly of the present invention can be produced according to a known method.

For example, examples of the method for producing a liposome include a probe technique and a bath technique in which an aqueous solvent is added to a single- or mixed-lipid film for hydration/swelling and subjected to ultrasonic treatment. Examples further include agitation (vortex mixing, homogenizer) techniques in which an aqueous solvent is added to a single- or mixed-lipid film before vortex treatment and subsequent ultrasonic treatment.

Alternatively, examples include ethanol injection techniques and ether injection techniques in which a single- or mixed-lipid is dissolved in an organic solvent, and the resulting solution is injected into an aqueous phase.

Alternatively, a liposome can be produced by dispersing a single- or mixed-lipid film into an aqueous phase, together with a non-ionic surfactant such as sodium cholate, sodium dodecyl sulfate, Triton X, octyl glucoside or lauryl ether to form an emulsion, which is then subjected to dialysis to remove the impurities.

Alternatively, there is a freeze-thaw technique in which an aqueous solvent is added to a single- or mixed-lipid film and vigorously suspended. The resulting solution is subjected to ultrasonic treatment. Subsequently, the resultant is subjected to liquid nitrogen for freeze-thaw.

Alternatively, there is a reverse phase evaporation technique (REV technique) in which a single- or mixed-lipid is dissolved in an organic solvent, a small amount of aqueous solvent is added to the resulting solution and ultrasonic vibration is applied thereto. Then, the organic solvent such as ethanol or ether is removed under reduced pressure or by dialysis, thereby producing a liposome.

The particle size of the liposome obtained as described above is adjusted by high-pressure extrusion (extrusion) method, French press method or the like.

Thus, a molecular assembly of the present invention containing a boron cluster-modified PEG lipid derivative as a structural lipid can be produced as described above.

According to a preferable embodiment of the present invention, the molecular assembly of the present invention can efficiently incorporate $^{10}$B nucleus contained in the boron cluster-modified PEG lipid derivative into a tumor tissue through use of a DDS. According to a preferable embodiment of the present invention, the molecular assembly of the present invention can favorably used for boron neutron capture therapy.

The molecular assembly of the present invention may be administered, for example, orally or, parenterally, like intravenously, transdermally, by inhalation or directly to a disease site. Any dose may be given as long as it is within an effective dose, which may vary depending on the target disease, administration target, administration method, symptoms and the like, but generally, it is about 1500 to about 7500 mg (lipid weight) per kg body weight.

Hereinafter, the present invention will be described by means of examples although the present invention should not be limited to these examples.

Example 1

Production of Boron Cluster-Modified PEG Lipid Derivative (1)

120 mg of SUNBRIGHT (registered trademark) SERIES DSPE-020MA (NOF CORPORATION), 40 mg of $^{10}$B enriched Sodium mercaptododecaborate (BSH) (Katchem spol. s r. o., Ltd.) and PBS (6 mL, pH7.0) were used in a 0.1M aqueous NaOH solution to give pH8.0, and reaction was allowed at room temperature for 3 hours. The reaction was carried out while confirming the degree of progression by high performance liquid chromatograph (HPLC).

Figure 3:
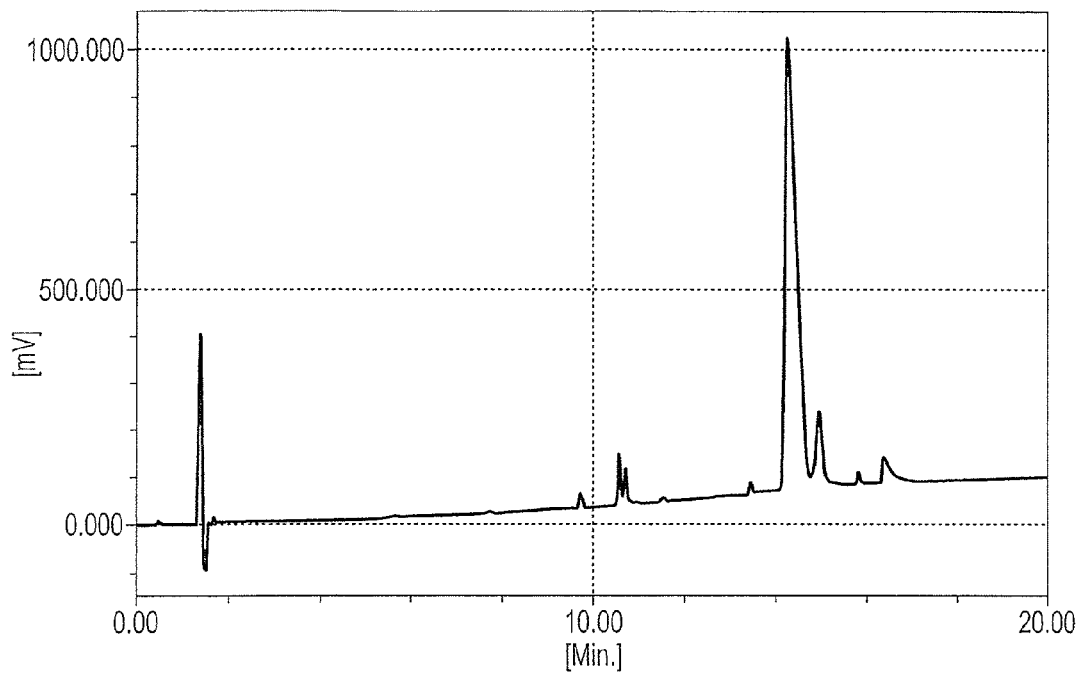
FIG. 3 A high performance liquid chromatograph of the compound obtained in Example 1.

Thereafter, the purity of the crude product was increased by dialysis (MWCO: 500-1000), and the resultant was freeze-dried to obtain the product of interest represented by the following formula. The purity and the yield of the product of interest were 81.7% (weight basis) and 115.4 mg, respectively, according to the results of the high performance liquid chromatograph (FIG. 3).

[Chemical Formula 4]

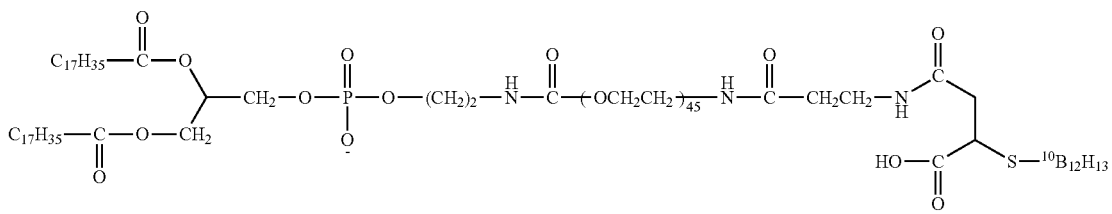

Conditions for dialysis and each of the reagents used for preparation of PBS were as follows.
Conditions for Dialysis:
External solution: ultrapure water
External solution exchange: 5 times/2 hours
Room temperature
Reagents Used for Preparation of PBS:
Sodium hydrogenphosphate dodecahydrate
Potassium dihydrogenphosphate
Sodium chloride
Potassium chloride
All of the above-mentioned reagents were obtained from SIGMA Aldrich.

The compound was identified by mass spectrum and high performance liquid chromatograph. The results are shown in FIGS. 2A, B and 3.

Figure 2A:
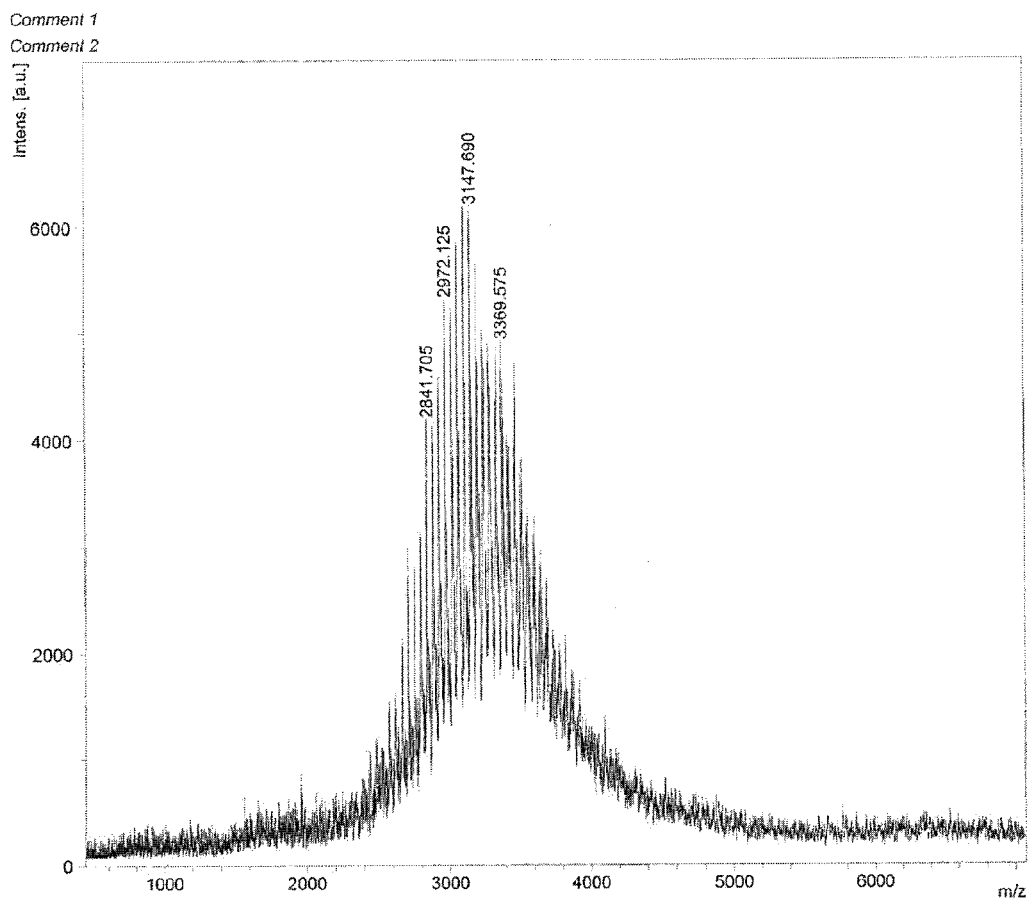
FIG. 2A A mass spectrum of the compound obtained in Example 1.
Figure 2B:
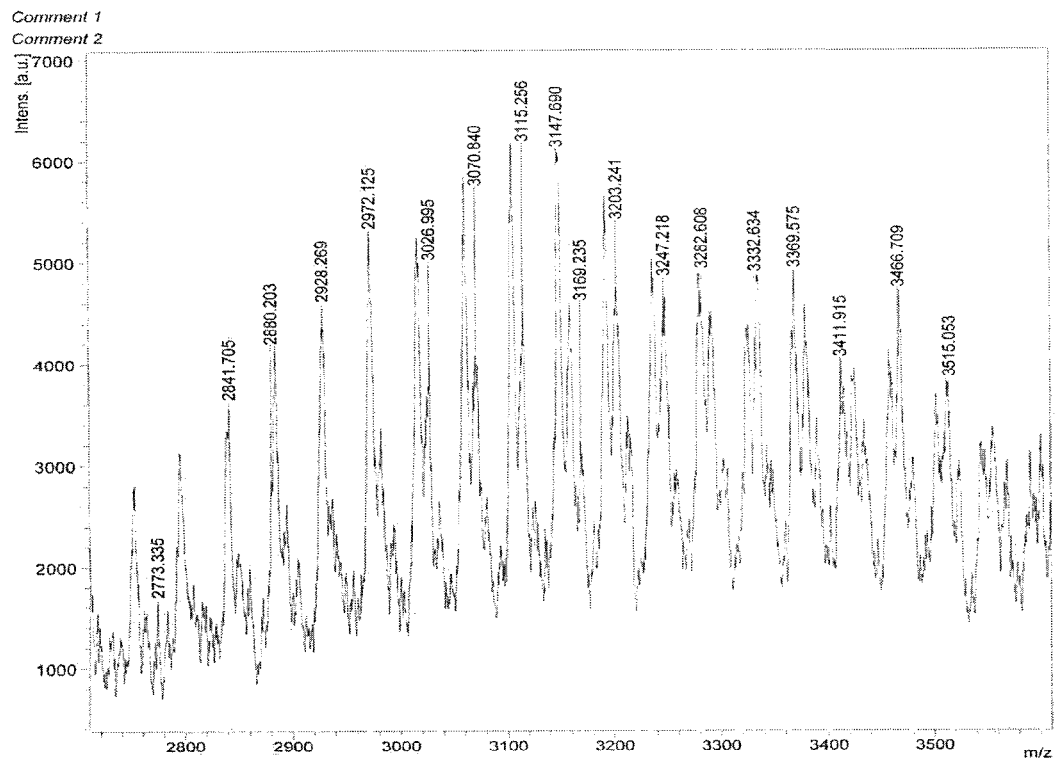
FIG. 2B An enlarged view of the peaks in the mass spectrum of the compound obtained in Example 1.

As shown in FIGS. 2A and B, while the exact mass of the present compound was 3146.07, the measured value of 3147.690 was confirmed. This means that the molecular weight error (%) was 0.08%, showing that the synthesis of the present compound was successful. Although there was a difference of 44 in the molecular weight regarding each of other peaks, this corresponds to 1 mer (—CH$_2$CH$_2$O—) of polyethylene glycol (PEG), supporting that the synthesis of the present compound was successful.

Moreover, as shown in FIG. 3, the measured value of the peak area was confirmed to be 81.71%. Thus, the present compound appears to have been obtained at a high purity by the above-described synthesis scheme.

Example 2

Preparation of Liposome

L-α-phosphatidylcholine distearoyl (DSPC), cholesterol (Chol) and the boron cluster-modified PEG lipid derivative (PEG-Boron-lipid) produced in Example 1 were used to prepare a mixed lipid at the composition ratio (molar ratio) shown in Table 1. The resultant was dissolved in an organic solvent (chloroform, methanol) to prepare a liposome by Bangham method. The resulting liposome was sized into 100 nm by extrusion, thereby preparing liposomes (1) to (4) containing the boron cluster-modified PEG lipid derivative at 5%, 10%, 15% or 20%, respectively.

TABLE 1

|  | DSPC | Chol | PEG-Boron-lipid |
|---|---|---|---|
| (1) PEG-Boron-lipid 5% liposome | 47.5 | 47.5 | 5 |
| (2) PEG-Boron-lipid 10% liposome | 45 | 45 | 10 |
| (3) PEG-Boron-lipid 15% liposome | 42.5 | 42.5 | 15 |
| (4) PEG-Boron-lipid 20% liposome | 40 | 40 | 20 |

Example 3

Incorporated Ratio of Boron Cluster-Modified PEG Lipid Derivative (PEG-Boron-Lipid) into Liposome For each of the liposomes prepared in Example 2, the incorporated ratio of the boron cluster-modified PEG lipid derivative into the liposome was examined by gel size exclusion chromatography.

Figure 4:
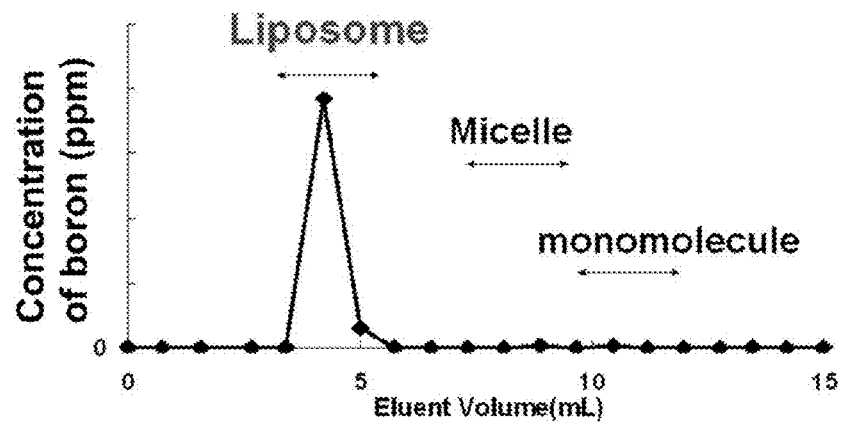
FIG. 4 A graph showing one example of the respective fractions resulting from separation by gel exclusion chromatography obtained in Example 3.

First, the liposome-mixed solution obtained in Example 2 was separated into a liposome fraction, a micelle fraction and a monomolecular fraction by gel size exclusion chromatography. An example showing these fractions is shown in FIG. 4.

Next, the concentration (ppm) of the boron atoms contained in the liposome fraction was determined with an inductively-coupled plasma emission spectrometer (ICP-AES) (Shimadzu Corporation, "ICPS-8100"). Based on the determined value, the incorporated ratio of the boron cluster-modified PEG lipid derivative into the liposome was calculated.

Figure 5:
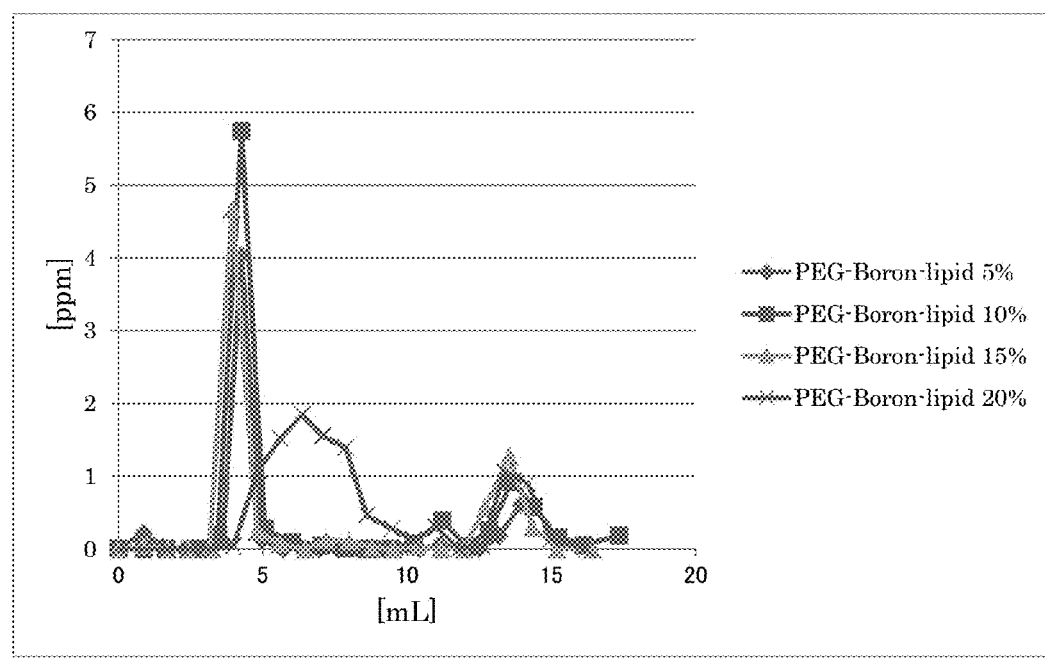
FIG. 5 A graph showing incorporated ratios of the boron cluster-modified PEG lipid derivative in the respective liposomes obtained in Example 3.

As a result, the boron cluster-modified PEG lipid derivative was found to be efficiency incorporated in each of the liposomes obtained in Example 2. The incorporated ratio of the boron cluster-modified PEG lipid derivative into each liposome obtained in Example 2 is shown in Table 2 and FIG. 5.

TABLE 2

| Lipid | Ratio of boron cluster-modified PEG lipid derivative (theoretical value) (mol %) | Incorporated ratio (%) |
|---|---|---|
| PEG-Boron-lipid-modified liposome | 5 | 79.2 |
|  | 10 | 68.5 |
|  | 15 | 66.8 |
|  | 20 | 24.5 |

Example 4

Physical Properties of Liposome

The particle size and the zeta potential of each monodispersed liposome comprising two or more of L-α-phosphatidylcholine distearoyl (DSPC), cholesterol (Chol), L-α-distearoyl-phosphatidylethanolamine (DSPE)-PEG2000 (DSPE-PEG2000) and the boron cluster-modified PEG lipid

[Chemical Formula 5]

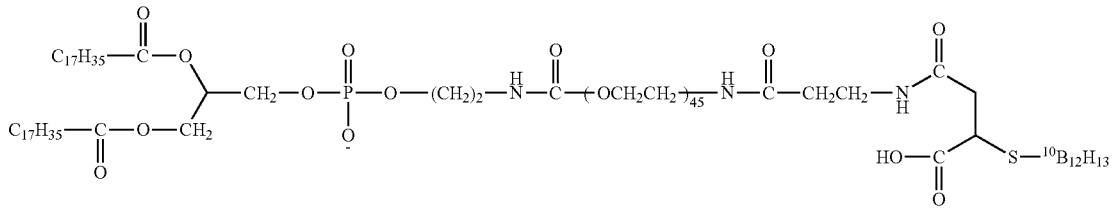

derivative produced in Example 1 were determined and compared by dynamic light scattering method (Zetasizer Nano ZS, manufactured by Malvern Instruments Ltd.). Similar to Example 2, each of the liposomes was prepared by a lipid-film technique followed by an extrusion technique. The results are shown in Table 3.

TABLE 3

| | DSPC/Chol/DSPE-PEG/PEG-Boron-lipid | Particle size (nm, u/G2) | Zeta potential (mV) |
|---|---|---|---|
| Unmodified liposome | 50/50/0/0 | 147 | −40 |
| PEG liposome | 47/47/6/0 | 143 | −15 |
| PEG-Boron-lipid 5% liposome | 47.5/47.5/0/5 | 168.8 | −42.3 |
| PEG-Boron-lipid 10% liposome | 45/45/0/10 | 125.7 | −36.5 |

As shown in Table 3, similar to PEG-modified liposome (PEG liposome), the liposomes of the present invention containing the boron cluster-modified PEG lipid derivatives (PEG-Boron-lipid 5% liposome or PEG-Boron-lipid 10% liposome) showed negative zeta potential. In addition, the particle sizes of the liposomes of the present invention were approximately 100 nm to 200 nm or less, showing that the particle sizes were controlled to give the highest EPR effect (enhanced permeability and retention effect).

Figure 6:
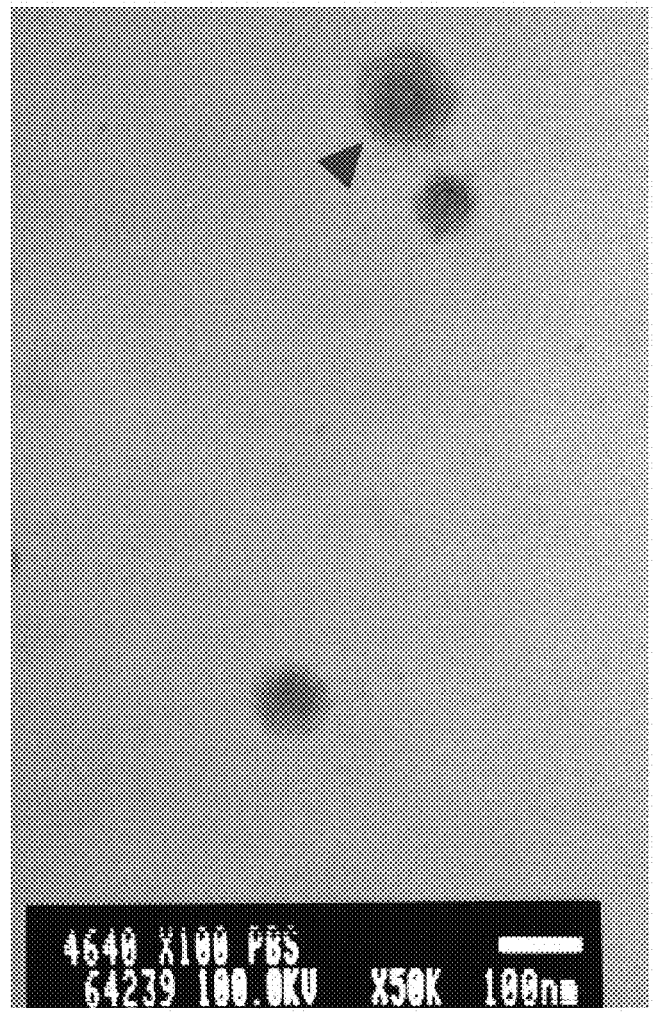
FIG. 6 A micrograph of a PEG-Boron-lipid 5% liposome taken with a transmission-type electron microscope (accelerating voltage: 100 kV).

FIG. 6 is a micrograph of the PEG-Boron-lipid 5% liposome taken with a transmission-type electron microscope (accelerating voltage: 100 kV) (in the figure, indicated by an arrow). As shown in FIG. 6, the PEG-Boron-lipid-modified liposome forms a bilayer lamellar and has a monolayer structure.

Example 5

Production of Boron Cluster-Modified PEG Lipid Derivative (2)

120 mg of SUNBRIGHT (registered trademark) SERIES DSPE-020MA (NOF CORPORATION), 40 mg of $^{10}$B enriched Sodium mercaptododecaborate (BSH) (Katchem spol. s r. o., Ltd.) and PBS (6 mL, pH7.0) were used in a 0.1M aqueous NaOH solution to give pH8.0, and reaction was allowed with light shielding at room temperature for 3 hours. The reaction was carried out while confirming the degree of progression by high performance liquid chromatograph (HPLC).

Thereafter, the purity of the crude product was increased by dialysis (MWCO: 500-1000), and the resultant was freeze-dried to obtain the product of interest represented by the following formula. The purity and the yield of the product of interest were 89.05% (weight basis) and 135.0 mg, respectively.

Conditions for dialysis and each of the reagents used for preparation of PBS were as follows.

Conditions for Dialysis:
External solution: ultrapure water
External solution exchange: 5 times/2 hours
Room temperature, light shielding
Reagents Used for Preparation of PBS:
Sodium hydrogenphosphate dodecahydrate
Potassium dihydrogenphosphate
Sodium chloride
Potassium chloride All of the above-mentioned reagents were obtained from SIGMA Aldrich.

The compound was identified by $^1$H-NMR, $^{10}$B-NMR, mass spectrum (time-of-flight mass spectrometry, TOF-MS) and high performance liquid chromatograph. The results are shown in FIGS. 7, 8, 9 and 10.

Figure 7:
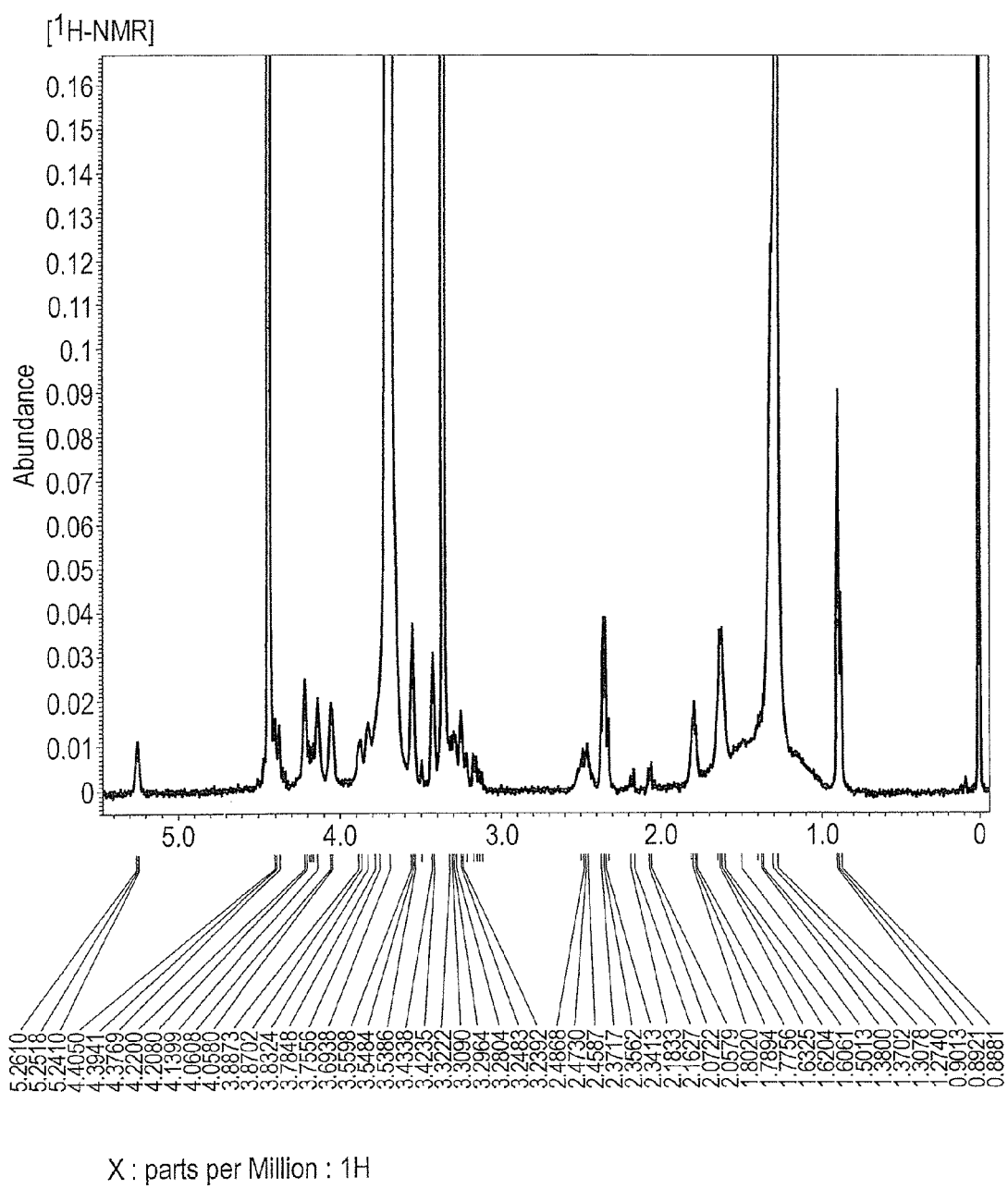
FIG. 7 A 1H-NMR spectrum chart of the compound obtained in Example 5.

As shown in FIG. 7, for the PEG-Boron-lipid, δ=0.89 [t, 6H], peak of the methyl group of the alkyl chain terminal (2CH$_2$CH$_3$), was observed, confirming two alkyl chains in the synthesized product.

Figure 8:
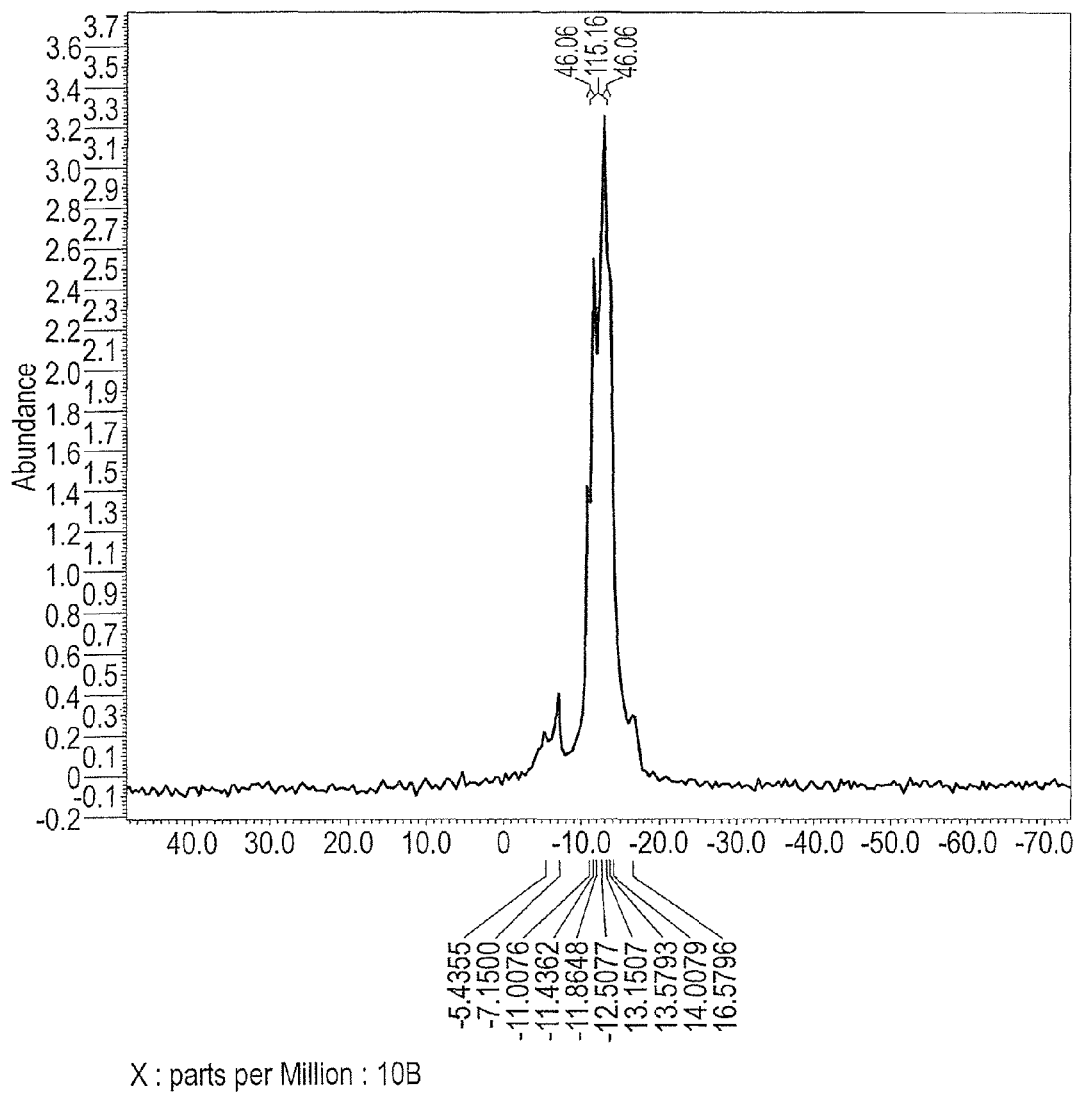
FIG. 8 A 10B-NMR spectrum chart of the compound obtained in Example 5.

As shown in FIG. 8, for the PEG-Boron-lipid, boron peak δ=−11 to δ=−16 was observed, confirming that the synthesized product was a boron compound.

Figure 9A:
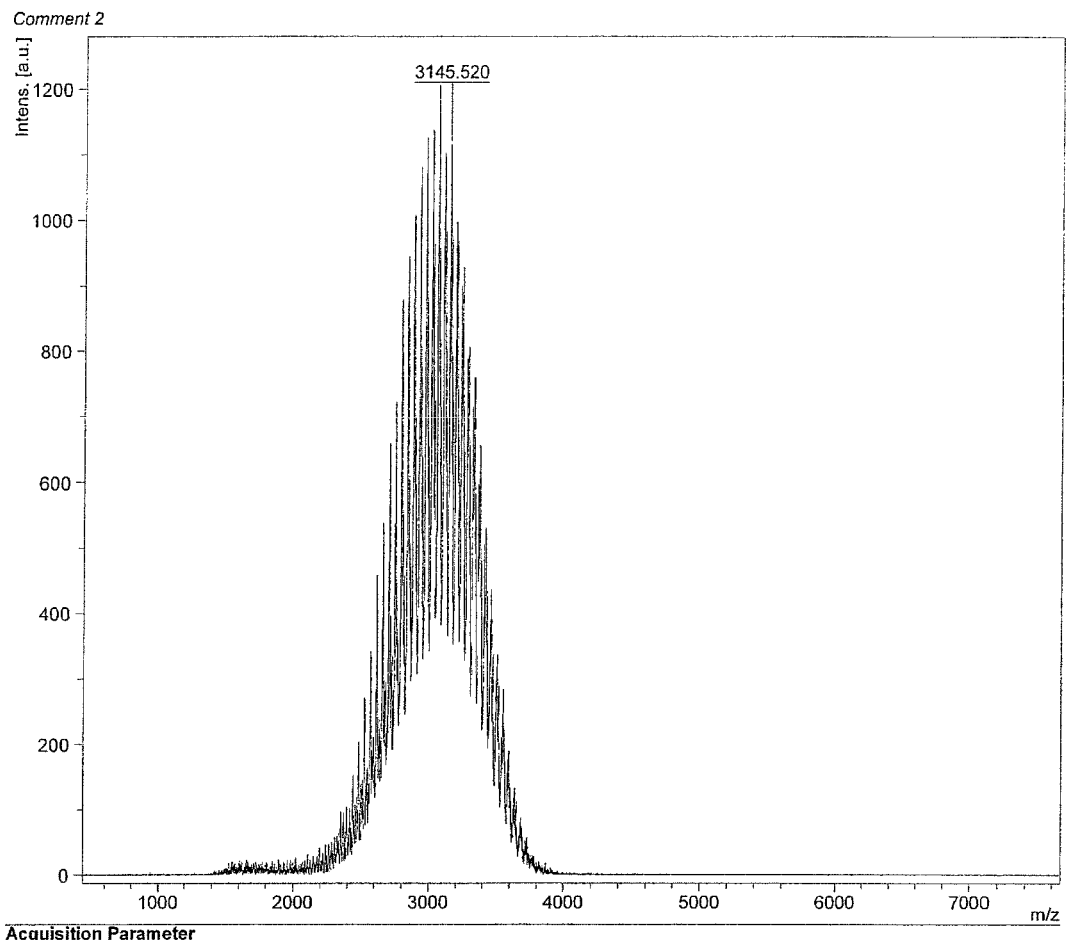
FIG. 9A A mass spectrum of the compound obtained in Example 5.
Figure 9B:
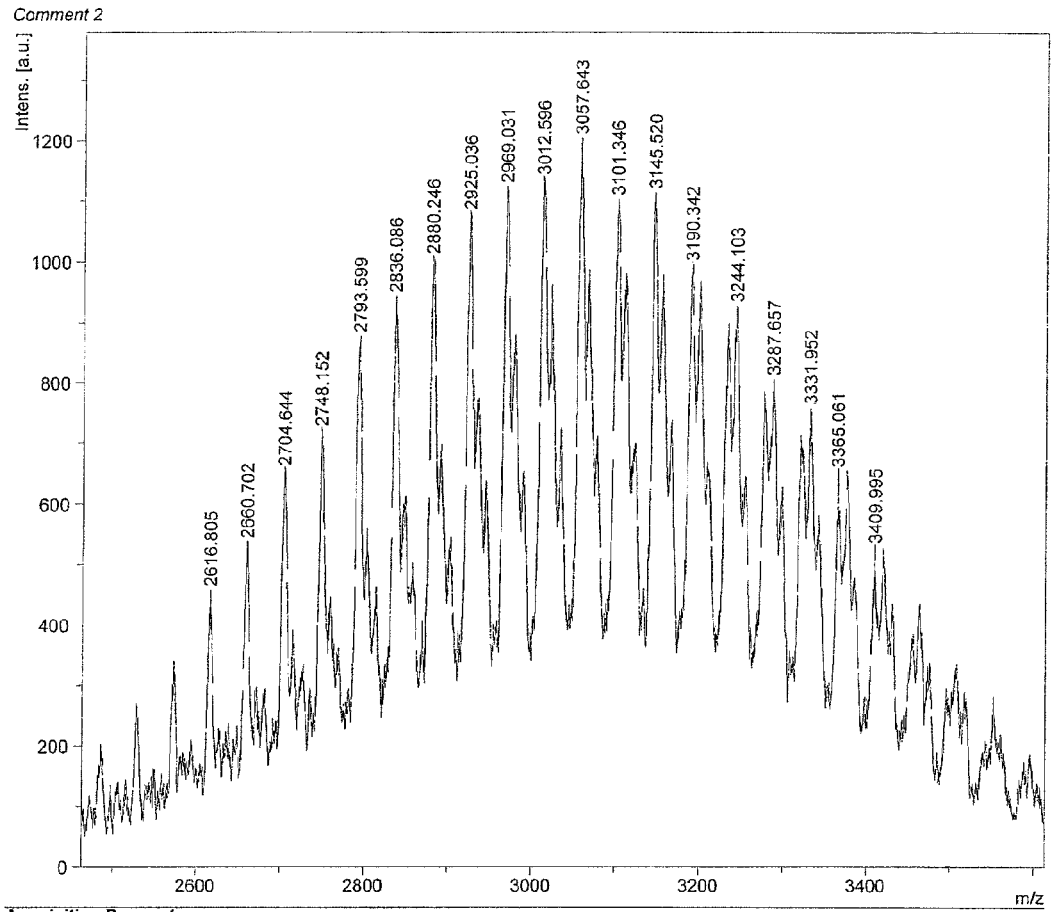
FIG. 9B An enlarged view of the peaks in the mass spectrum of the compound obtained in Example 5.

In addition, as shown in FIGS. 9A and 9B, while the exact mass of the present compound was 3146.07, the measured value of 3145.520 was confirmed. This means that the molecular weight error (%) was 0.017%, showing that the synthesis of the present compound was successful. Although there was a difference of 44 in the molecular weight regarding each of other peaks, this corresponds to 1 mer (—CH$_2$CH$_2$O—) of polyethylene glycol (PEG), supporting that the synthesis of the present compound was successful.

Figure 10:
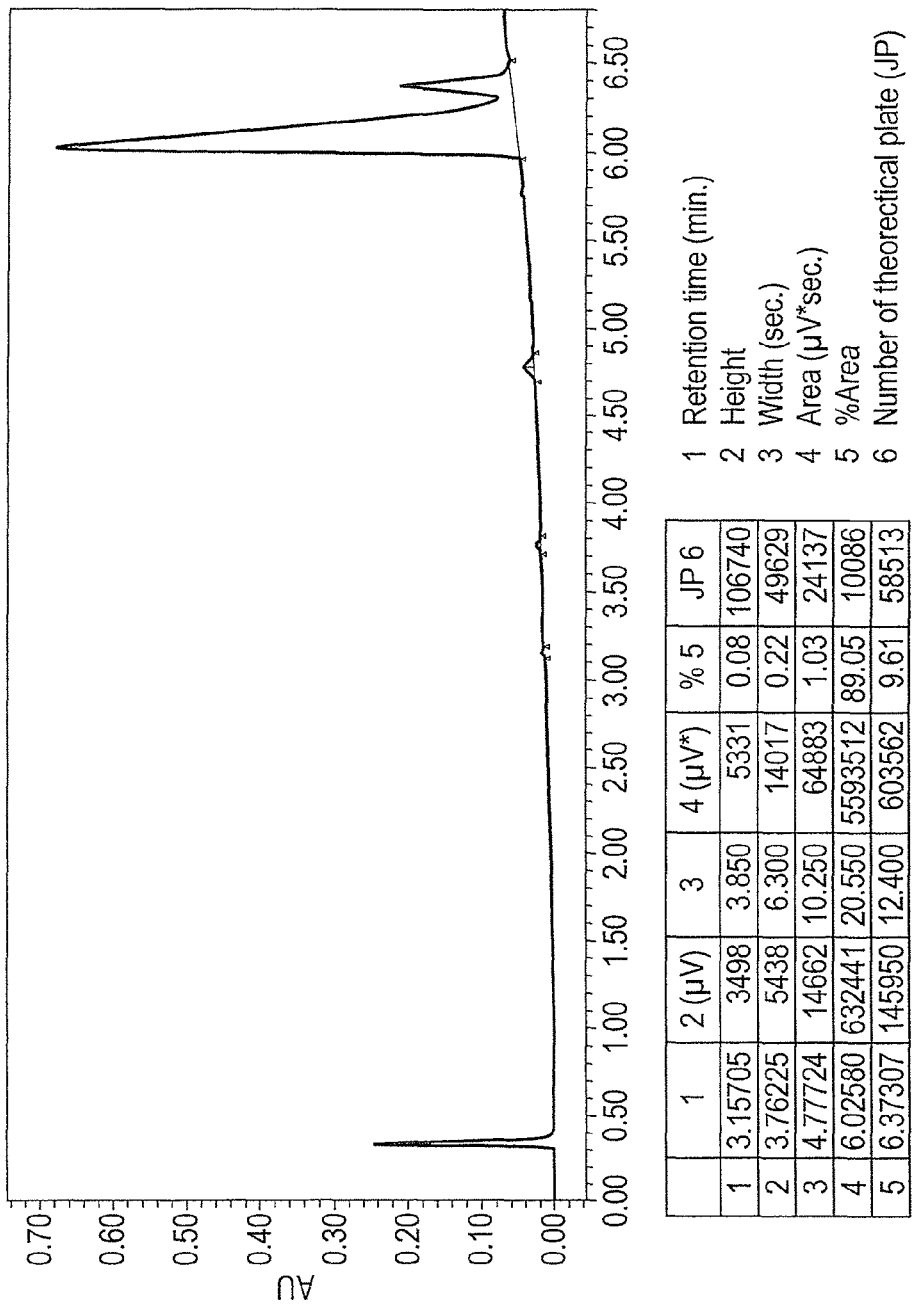
FIG. 10 A high performance liquid chromatograph of the compound obtained in Example 5.

Moreover, as shown in FIG. 10, the measured value of the peak area was confirmed to be 89.05%. Thus, the present compound appears to have been obtained at a high purity by the above-described synthesis scheme.

Example 6

Influence of Neutron Beam Irradiation on Normal Cells (In Vitro)

Figure 11:
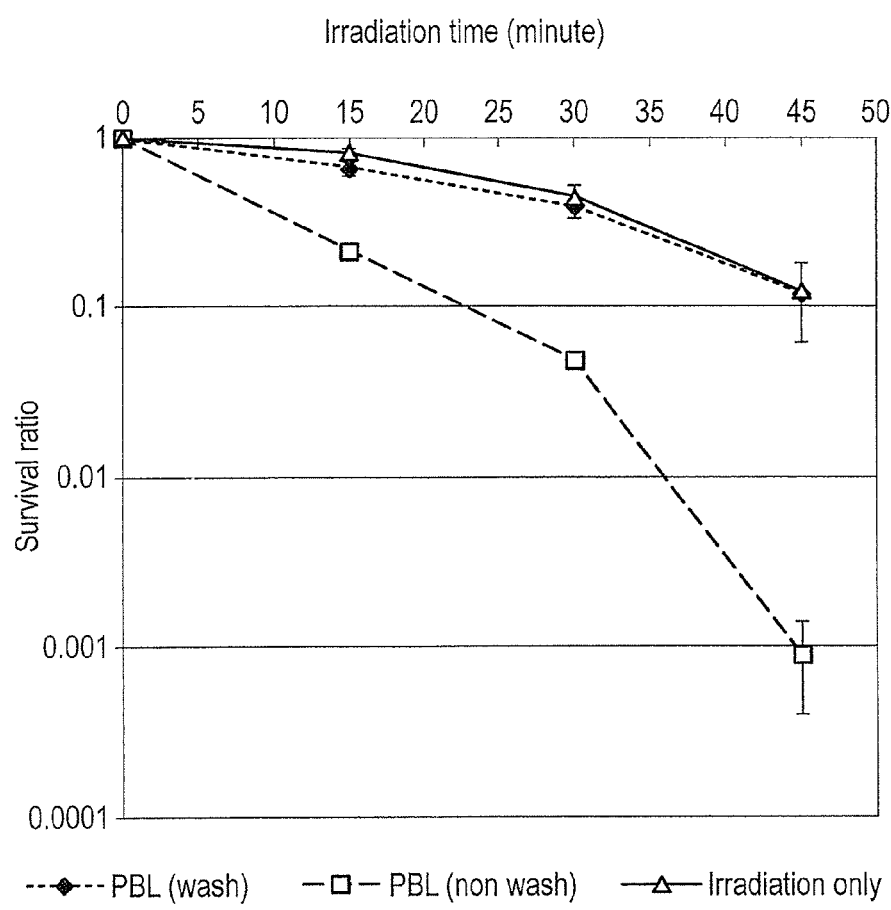
FIG. 11 A graph showing the cytotoxicity reactions upon irradiating the PEG-Boron-lipid modification liposomes with a thermal neutron beam.

Influence of the neutron beam irradiation on normal cells (in vitro) was examined by the following procedure. The cell line used for the examination was V79 379A (classification; normal).
<Method>
A liposome suspension prepared at a lipid composition ratio of (DSPC:Chol:PEG-Boron-lipid=1:1:0.12) and a lipid concentration of 50 mg/mL by ultrasonic treatment was subjected to ultracentrifugation (100,000×g, 2 hours, 4° C.). The resulting PEG-Boron-lipid 5% liposome was used. Neutron beam irradiation was performed with KUR. Irradiation at $2.65 \times 10^{12}$ thermal neutron/cm$^2$ was performed for respective times (15, 30 and 5 minutes). Following irradiation, Giemsa stain solution was used to conduct colony formation assay. Two samples used for irradiation were as follows.
(1) Wash
V79 379A cells (4×10$^5$ cells) were seeded in a 25T flask and cultured at 37° C., under 5% $CO_2$ conditions for 6 hours. 6 hours later, the medium was exchanged. 1 mL of the PEG-Boron-lipid 5% liposome solution was added to 4 mL of a fresh culture solution and cultured at 37° C., under 5% $CO_2$ conditions for 2 hours. 2 hours later, the medium was removed, washed with PBS, and then added with trypsin to peel off the cells. The cells were precipitated by centrifugation. The supernatant was removed and the resultant was added with 2 mL of a fresh culture solution to obtain a cell suspension. From 2 mL of the cell suspension, 500 µL, was dispensed into a Cryo tube to make a single sample.
(2) Non Wash
V79 379A cells (4×10$^5$ cells) were seeded in a 25T flask, and cultured at 37° C., under 5% $CO_2$ conditions for 6 hours. 6 hours later, the medium was removed, washed with PBS, and then added with trypsin to peel off the cells. The number of cells was counted. The cells were precipitated by centrifugation. The supernatant was removed and the resultant was added with 1 mL of a fresh culture solution to obtain a cell suspension. 250 µL of V79 379A cells (1×10$^5$ cells) were dispensed into a Cryo tube, added with 250 µL, of the PEG-Boron-lipid 5% liposome solution, and cultured for 2 hours to obtain a cell suspension to be used as a single sample.
<Results>
As shown in FIG. 11, as compared to the group with neutron beam irradiation only (irradiation only), the group that went through wash (1) (PBL (wash)) after adding the PEG-Boron-lipid 5% liposome to V79 379A cells only showed a cytocidal effect similar to that of the neutron beam irradiation only group, confirming that there was no significant difference by the addition of the PEG-Boron-lipid 5%-modified liposome. Student's t test was employed as the test. Furthermore, in the group that went through non-wash (2) (PBL (non wash)), a cytocidal effect was observed upon neutron beam irradiation, confirming that the PEG-Boron-lipid 5%-modified liposome contained $^{10}$B-enriched boron atom group.

A toxicity experiment with normal cells was conducted with V79 379A whose classification was normal cells. As a result, PEG-Boron-lipid seems to gain a cytocidal effect only by neutron irradiation.

Example 7

Determination of Antitumor Effect by Neutron Irradiation (In Vivo)

An antitumor effect of the neutron beam irradiation was determined by the following procedure (in vivo).
<Method>
A PEG-Boron-lipid 5% liposome prepared in the same manner as in Example 6 was administered to cancer-carrying mice so as to examine the BNCT therapeutic effect thereof. The cancer-carrying models were prepared by seeding mouse colon cancer cells (CT26, 5×10$^6$ cells) to the right thighs of BALB/cA mice (female, 4 weeks old, weighing 16-20 g) to have a tumor diameter of 6-8 mm (about 8 days after the injection). An isoflurane inhalation anesthesia apparatus was used for the mice upon experiment so that the procedure took place without pain. In conjunction of the series of animal experiments, the plan document of the animal experiments was submitted in advance to the Animal Experiment Committee, University of Tsukuba so as to get approval as a plan that complies with the regulations and the rules for experiments and that also take into account about pain of the animals and else. In addition, similar procedure was taken through application to the Kyoto University for joint use.

PEG-Boron-lipid 5% liposome was injected to the tail vein of the prepared cancer-carrying mouse at 10 mg $^{10}$B/kg, and, after 24 hours, neutron beam irradiation was conducted with KUR. The neutron beam dose was 4.5 to $7.0 \times 10^{12}$ neutrons/cm$^2$.

The tumor diameter was determined over time after the irradiation until Day 21 so as to compare the effect of inhibiting tumor growth with the control group. A BSH solution group (BSH, 6 cases), a group with irradiation of neutron beam only (irradiation only, 6 cases) and a group with no drug administration/no irradiation (no treatment, 12 cases) were used as controls for comparison and examination. The tumor sizes were determined according to the following formula.

(Long diameter (mm))×(Short diameter (mm))$^2$=tumor size (mm$^3$)

Figure 12:
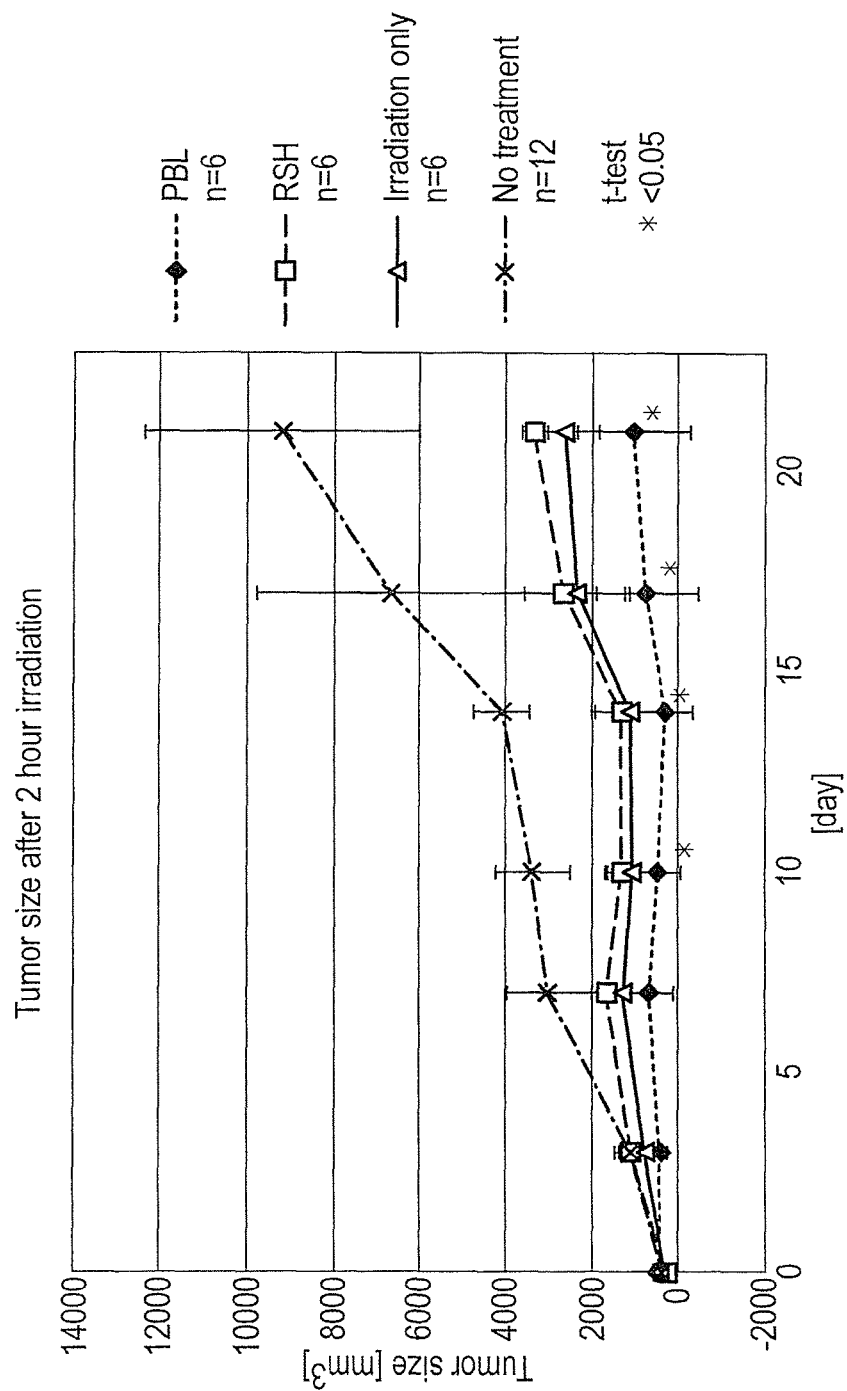
FIG. 12 A graph showing the antitumor effects upon irradiating the PEG-Boron-lipid modification liposomes with a thermal neutron beam.

<Results>
As shown in FIG. 12, the PEG-Boron-lipid-modified liposome significantly inhibited the tumor growth as compared to all of the other groups on Days 10, 14, 17 and 21. In particular, the tumor did not grow until Day 14. Moreover, among the 6 cases of PEG-Boron-lipid 5% liposome administration group, complete disappearance of the tumor was confirmed for one case.

The effect of inhibiting tumor growth was confirmed only by the results from the comparison with BSH in FIG. 12. However, since the results were better than the BSH used as clinical cases, the effect is considered to be high.

INDUSTRIAL APPLICABILITY

A boron cluster-modified PEG lipid derivative of the present invention is useful as a drug carrier that allows boron delivery. According to a preferable embodiment of the present invention, a molecular assembly of the present invention containing said PEG lipid derivative is highly likely to realize an increase in the boron concentration in a tumor and low accumulation in normal cells upon use of DDS, and thus is expected for its use as a boron carrier compound for boron neutron capture therapy for cancer.

The invention claimed is:

1. A boron cluster-modified PEG lipid derivative represented by Formula (I):

[Chemical Formula 6]

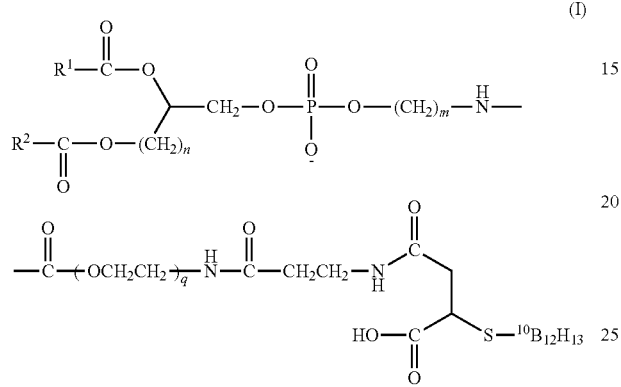

wherein, m and n are each independently an integer of 1-4, q is an integer of 1-280, and $R^1$ and $R^2$ are each independently a hydrocarbon group with a carbon number of 8-22.

2. The PEG lipid derivative according to claim 1, wherein $R^1$ and $R^2$ are each independently a linear or branched alkyl group with a carbon number of 12-22.

3. The PEG lipid derivative according to claim 1, wherein m is 2 and n is 1.

4. A molecular assembly comprising the PEG lipid derivative according to claim 1.

5. The molecular assembly according to claim 4, wherein the PEG lipid derivative is contained at 2-20% in a molar ratio with respect to the total structural lipid of the molecular assembly.

6. The molecular assembly according to claim 4, further comprising L-α-phosphatidylcholine distearoyl and cholesterol.

7. The molecular assembly according to claim 4, which is a liposome.

8. The molecular assembly according to claim 7, wherein the particle size of the liposome is 50-400 nm as measured by a dynamic light scattering method.

9. The PEG lipid derivative according to claim 2, wherein m is 2 and n is 1.

10. A molecular assembly comprising the PEG lipid derivative according to claim 2.

11. A molecular assembly comprising the PEG lipid derivative according to claim 3.

12. The molecular assembly according to claim 10, wherein the PEG lipid derivative is contained at 2-20% in a molar ratio with respect to the total structural lipid of the molecular assembly.

13. The molecular assembly according to claim 11, wherein the PEG lipid derivative is contained at 2-20% in a molar ratio with respect to the total structural lipid of the molecular assembly.

14. The molecular assembly according to claim 5, further comprising L-α-phosphatidylcholine distearoyl and cholesterol.

15. The molecular assembly according to claim 5, which is a liposome.

16. The molecular assembly according to claim 6, which is a liposome.

* * * * *